United States Patent [19]

Corn, Jr. et al.

[11] 4,049,721

[45] Sept. 20, 1977

[54] PURIFICATION OF CRUDE 9,9-BIS-(4-HYDROXYPHENYL)-FLUORENE

[75] Inventors: John E. Corn, Jr., Mt. Vernon, Ind.; Howard J. Klopfer, Clifton Park, N.Y.

[73] Assignee: General Electric Company, Schenectady, N.Y.

[21] Appl. No.: 720,744

[22] Filed: Sept. 7, 1976

[51] Int. Cl.² .............................................. C07C 37/24
[52] U.S. Cl. .......................... 260/619 A; 260/619 R; 260/619 D; 260/619 F
[58] Field of Search ........... 260/619 F, 619 D, 619 R, 260/619 A

[56] References Cited

PUBLICATIONS

Morgan, "Macromolecules", vol. 3, p. 536 (1970).

*Primary Examiner*—Norman Morgenstern
*Attorney, Agent, or Firm*—Joseph T. Cohen; Jerome C. Squillaro

[57] ABSTRACT

Certain impurities found in 9,9-bis(4-hydroxyphenyl)-fluorene are removed by treatment of the latter with a methanol-water mixture and thereafter isolating the purified fluorene.

2 Claims, No Drawings

PURIFICATION OF CRUDE 9,9-BIS-(4-HYDROXYPHENYL)-FLUORENE

This invention is concerned with a process for purifying a bisphenol fluorene. More particularly, the invention is concerned with improving the color of and removing from 9,9-bis(4-hydroxyphenyl)-fluorene (hereinafter called BPF) having the formula

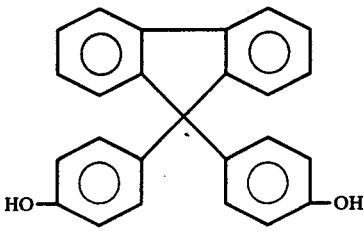

residual phenol used to make the BPF by treatment of the impure BPF with a methanol-water mixture in which the impurities are soluble, and thereafter isolating the desired BPF.

The Government has rights in this invention pursuant to Contract No. N00019-76-C-0096 awarded by the Department of the Navy.

The above-identified BPF of formula I can be prepared in the manner disclosed by P. W. Morgan in *Macromolecules,* Volume 3, page 536 (1970), whereby fluorenone is reacted with phenol in the presence of β-mercaptopropionic acid and anhydrous HCl. When this reaction is carried out, it is found that a good yield of desired BPF is obtained, but it is contaminated by both residual phenol and excessive coloration.

BPF can be used to make various polymer compositions. For instance, the BPF can be reacted with phosgene to make polycarbonate resins, or else it can be reacted with organic acyl dihalides such as terephthaloyl chloride, isophthaloyl chloride, etc., to make polyester resins. Alternatively, the BPF can be reacted with nitro-N-methylphthalimides in the manner described in U.S. Pat. No. 3,944,583 of Clayton B. Quinn, issued Mar. 16, 1976, to form intermediate precursors which upon further processing can yield novel dianhydrides. The latter can in turn be reacted with organic diamines to make polyimide resins of the type more particularly disclosed and claimed in U.S. Pat. No. 3,968,083, issued July 6, 1976, of the aforesaid Clayton B. Quinn. By reference these two patents, both of which are assigned to the same assignee as the present invention, are made part of the disclosures and teachings of the instant application. Resinous compositions obtained from the BPF have been found to have good flammability resistance and oxygen indices, which make them useful in applications where resistance to elevated temperatures is desirable, for instance, as insulation for electrical conductors, as motor slot liners, as films, and as high temperature coatings.

When using the BPF, it is important that any impurities be significantly reduced and preferably removed from the BPF since the presence of the impurities results in low molecular weight products when the BPF is used for polymer formation. This interferes with obtaining compositions of the desired properties required for molding, extruding, or other applications. In addition, the color of the BPF has profound effect on the color of molded parts, and if colorless (or near colorless) products are to be obtained, the phenol residually present should be removed from the BPF before processing into resins.

Prior art methods for purifying the BPF have been unsatisfactory and impractical for commercial use. For instance, in the aforesaid Morgan article in *Macromolecules,* Morgan points out that the BPF can be isolated by either dilution of the reaction mixture with water or by steam distillation to remove the excess phenol and other volatiles. However, attempts to follow these procedures have encountered problems because the dilution of the reaction mixture water does indeed yield a solid, but it is a sticky solid difficult to handle in larger quantities, for instance, greater than 150 grams. When steam distillation is resorted to, a sticky solid is also obtained. In addition, these methods of purification seem to cause an increase in the color of the desired product, and the fact that sticky solids are obtained prevents attempts to crystallize the mass and obtain the pure BPF. Thus, in addition to reducing the color in the BPF, it is also essential, for future processing of the BPF, that the BPF be obtained in the form of the more desirable free-flowing form.

We have now discovered that we are able to remove color and essentially all the residual phenol from the BPF by employing a methanol-water treatment as a means for extracting the impurities in a simple step to leave behind the desired BPF of the requisite purity and in free-flowing form. In accordance with our invention, the BPF containing the aforesaid inpurities is mixed with methanol (room temperature usually being adequate), preferably in an amount sufficient to solubilize all of the impurities therein. This mixture is then filtered to remove solid material, water is then added to the filtrate, and the filtrate containing the BPF as a suspension is heated, e.g., to temperatures of 65° to 90° C. (usually reflux temperatures are sufficient) to effect complete solution, and then cooling the mixture to below 30° C., at which point the BPF will settle out as a white crystalline material. Removal and washing of the latter with watermethanol will give essentially color-free BPF free of the above-mentioned impurity. The color will approach water-white as contrasted to tan or dark yellow if the methanol-water treatment is omitted.

The amount of methanol used can vary widely but advantageously, by weight, should be within the range of from 1 to 5 or more parts of methanol, per part of the crude BPF mixture. The amount of water used with the methanol can vary widely but should be, on a weight basis, within the range of from 0.5 to 2.0 parts water per part methanol. If desired, further recrystallization may be carried out from nitromethane as shown in the copending application of John E. Corn, Ser. No. 667,461, filed Mar. 16, 1976 and assigned to the same assignee as the present invention; but, in either event, a free-flowing white powder will be obtained.

In order that those skilled in the art may better understand how the present invention may be practiced, the following example is given by way of illustration and not by way of limitation.

The color index and color code referred to in the following example is a method of color classification originated in the General Electric Company Research and Development Center and is designed to avoid or eliminate some of the deficiencies found in known color scale indices such as those used under the term "APHA" (American Public Health Association) color scale and the "Yellowness Index" method described by J. M. Fitzgerald in the book *Analytical Photochemistry and Photochemical Analysis*, page 268, published by M. Dekker (1971).

Two formulas are used to determine the color index (amount of yellowness) and color code (intensity of color present, such as yellow, orange, blue). These formulas are as follows:

$$(10[A_{436} + A_{490} + A_{546} + A_{570} + A_{620} + A_{660}]) = \text{color index}$$

$$10 \frac{([A_{436} + A_{490} + A_{546}] - [A_{570} + A_{620} + A_{660}])}{\text{color index}} = \text{color code}$$

where color index is representative of the amount of color in a sample and color code is representative of the hue of a sample. A is the spectrophotometric absorbance at the wavelength in nM indicated by the subscript.

EXAMPLE 1

To a reaction vessel equipped with stirrer, thermometer, gas inlet tube, reflux condenser, and nitrogen bypass was placed 2720 grams fluorenone (15.094 moles), 5684 grams phenol (60.40 moles), and 20.60 grams β-mercaptopropionic acid (0.1943 mole), the latter being used as a catalyst. While under a nitrogen atmosphere, the reaction mixture was heated to about 86° C. to effect complete solution of the ingredients. Forty grams (1.096 moles) HCl gas was bubbled into the solution while the external heating was stopped. The exothermic reaction carried the solution temperature to 98° C. over the next 40 minutes. The reaction mixture was heated at 90° C. for 8 hours and cooled to room temperature, at which point solid BPF settled out of solution. The procedure up to this point is substantially the same as that used in the Morgan article mentioned previously.

The reaction mixture was then dissolved in 8000 ml methyl alcohol and filtered. The filtrate was placed in a large container and 7500 ml water was added with stirring. The reaction mixture was heated to reflux (about 84° C.) to effect a clear solution, and allowed to cool slowly while seeding the mixture with some BPF. The white crystals which formed were isolated by filtration, washed on the filter with 800 ml methanol-water (1:1 by volume) and dried at 60° C. under vacuum. There was a considerable amount of color left behind in the filtrate. No attempt was made to obtain a second crop of crystals from the filtrate. The almost pure white, free-flowing crystals thus obtained were recrystallized from nitromethane to obtain 2567.2 grams of essentially pure BPF. Concentration and recrystallization of the mother liquor yielded an additional 592 grams for an overall yield of about 60%. Compared to the color of the BPF obtained by previous methods, and particularly by the method used in the aforementioned Morgan article, the crystalline BPF in this example using the methanol treatment was considerably less colored.

To further emphasize the advantages as established by the color index and color code tests described above, three samples of the formed BPF up to the methanol step were treated in different manners and the color index and color code determined in each case using the formulas referred to above. The following table shows the results of these tests:

TABLE

| Test No. | Isolation Method | Color Index | Color Code |
|---|---|---|---|
| 1 | Azeotropic distillation with decane. Recrystallized once from nitromethane | 18.77 | 7.01 |
| 2 | Dissolved in methanol, treated twice with activated charcoal. | 2.78 | 7.97 |
| 3 | Methanol-water crystallization from reaction mixture according to claimed invention. Recrystallized once from nitromethane. | 2.06 | 5.05 |

It should be noted from the above numbers that the higher the color index, the more the intensity of the yellow color. Also the lower the color code, the less of a hue is present in the sample. The above data shows that BPF made and purified by previous methods is more highly colored than the one described in the instant application even after treatment with decolorizing charcoal. In addition, any traces of phenol were completely eliminated as a result of the methanol-water treatment.

The fact that BPF of improved color is obtained by our invention in the isolation of the BPF monomer, carried over into the polymers which may be made therefrom. Thus, when BPF purified in the manner described above using the methanol-water step was subjected to treatment with phosgene in pyridine to form the polycarbonate resin, it was found that the color index and the color code of the polymer using the methanol-purified BPF were lower than the same color index and color code for BPF which was used for polymerization purposes after it was prepared in the manner described in the above-mentioned Morgan article without subjecting it to our above-described methanol treatment. Specifically, whereas the values for the color index and color code, respectively, for the polycarbonate made from the BPF in pyridine produced in accordance with the Morgan article were 3.80 and 6.05, the same values for the polycarbonate prepared from the BPF purified with the methanol-water had values, respectively, 1.60 and 5.00.

What we claim as new and desire to secure by letters patent of the United States is:

1. The process for purifying crude 9,9-bis(4-hydroxyphenyl)-fluorene containing phenol as an impurity therein, which process comprises (1) mixing the aforesaid impure fluorene with an amount of methanol sufficient to solubilize all the impurity therein, (2) removing by filtration any solid material present in the aforesaid mixture, (3) adding water to the filtrate, (4) heating the mixture of the water and the filtrate to an elevated temperature to effect solubilization of the suspended material present in (3), (5) cooling the mixture to precipitate essentially pure 9,9-bis(4-hydroxyphenyl)-fluorene, and (6) separating the latter from the liquid containing the impurity therein.

2. The process as in claim 1 wherein, on a weight basis, the methanol comprises from 1 to 5 parts thereof per part of the crude fluorene and the water comprises from 0.5 to 2.0 parts of the latter per part of the methanol.

* * * * *